United States Patent
Bildstein et al.

(10) Patent No.: US 7,589,223 B2
(45) Date of Patent: Sep. 15, 2009

(54) POLYMERIZATION CATALYSTS, PREPARATION OF POLYOLEFINS, ORGANOTRANSITION METAL COMPOUNDS AND LIGANDS

(75) Inventors: Benno Bildstein, Innsbruck (AT); Alexander Krajete, Porsgrunn (NO)

(73) Assignee: Basell Polyolefine GmbH, Wesseling (DE)

(*) Notice: Subject to any disclaimer, the term of this patent is extended or adjusted under 35 U.S.C. 154(b) by 0 days.

(21) Appl. No.: 10/573,228

(22) PCT Filed: Sep. 16, 2004

(86) PCT No.: PCT/EP2004/010377
§ 371 (c)(1), (2), (4) Date: Mar. 24, 2006

(87) PCT Pub. No.: WO2005/030813
PCT Pub. Date: Apr. 7, 2005

(65) Prior Publication Data
US 2007/0004884 A1   Jan. 4, 2007

Related U.S. Application Data

(60) Provisional application No. 60/515,922, filed on Oct. 29, 2003.

(30) Foreign Application Priority Data
Sep. 25, 2003 (DE) ................. 103 44 659

(51) Int. Cl.
- C07F 15/00 (2006.01)
- C07F 13/00 (2006.01)
- C07F 11/00 (2006.01)
- C07F 9/00 (2006.01)

(52) U.S. Cl. ........................ 556/32; 556/138
(58) Field of Classification Search .......... 556/32, 556/138
See application file for complete search history.

(56) References Cited

U.S. PATENT DOCUMENTS

| | | |
|---|---|---|
| 6,417,302 B1 | 7/2002 | Bohnen |
| 6,589,905 B1 | 7/2003 | Fischer et al. |
| 6,828,454 B2 | 12/2004 | Kristen et al. |

FOREIGN PATENT DOCUMENTS

| | | |
|---|---|---|
| DE | 219 479 | 3/1985 |
| EP | 1 336 615 | 8/2003 |
| WO | WO-91/09882 | 7/1991 |
| WO | WO-96/00243 | 1/1996 |
| WO | WO-96/23010 | 8/1996 |
| WO | WO-98/27124 | 6/1998 |
| WO | WO-98/40419 | 9/1998 |
| WO | WO-99/06414 | 2/1999 |
| WO | WO-00/05277 | 2/2000 |
| WO | WO-00/31090 | 6/2000 |
| WO | WO-03/022889 | 3/2003 |

OTHER PUBLICATIONS

Britovsek, George J. P. et al., "The Search for New-Generation Olefin Polymerization Catalysts: Life Beyond Metallocenes", Angew. Chem. Int. Ed. 38 (1999), pp. 428-447.
Brintzinger, Hans-Herbert et al., "Stereospezifische Olefinpolymerisation mit chiralen Metallocenkatalysatoren", Angew. Chem. 107 (1995), pp. 1255-1283.
Britovsek, George J. P. et al., "Auf der Suche nach einer neuen Generation von Katalysatoren zur Olefinpolymerisation: "Leben" jenseits der Metallocene", Angew. Chem. 111 (1999), pp. 448-468.
Smith, Richard D. et al., "Amidrazones. I. The Methylation of Some Adimrazones and Hydrazide Imides", J. Org. Chem., 36(8)(1971), pp. 1155-1158.
Sadek, Elham M. et al., "Catalytic Polymerization of Methyl Methacrylate in Different Media Using Supported Metal Phthalocyanines, 1, Bulk Polymerization in Relation to the Microcrystalline Structure of Supported Metal Phthalocyanines", Macromol. Chem. Phys. 202 (2001), pp. 1505-1512.
Krajete, Alexander et al., "Iminohydroxamato Early and Late Transition Metal Halide complexes—New Precatalysts for Aluminoxane-Cocatalyzed Olefin Insertion Polymerization", Eur. J. Inorg. Chem. (2004), pp. 1740-1752.
Long, Gregory S. et al., "Transition Metal Phthalocyanine and Porphyrin Complexes as Catalysts for the Polymerization of Alkenes", Can. J. Chem. 79 (2001, pp. 1026-1029.

*Primary Examiner*—Caixia Lu
(74) *Attorney, Agent, or Firm*—Jarrod Raphael; William R. Reid; Jonathan L. Schuchardt

(57) ABSTRACT

The invention relates to non-metallocene catalyst systems useful for preparing olefin homopolymers or copolymers. The catalyst systems comprise a cocatalyst and a Group 3-10 transition metal compound that incorporates a diimine ligand in which $sp^2$-hybridized carbons of the imine groups are joined by a specific divalent one- or two-membered bridge (Y) comprising nitrogen and/or oxygen. The invention includes the diimine ligands, the transition metal compounds, the catalyst systems, and processes for making the ligands, transition metal compounds, catalyst systems, and olefin homopolymers or copolymers.

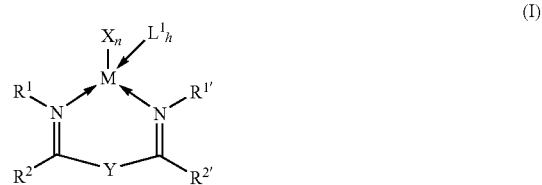

(I)

2 Claims, No Drawings

POLYMERIZATION CATALYSTS, PREPARATION OF POLYOLEFINS, ORGANOTRANSITION METAL COMPOUNDS AND LIGANDS

RELATED APPLICATIONS

This application is a national stage application (under 35 U.S.C. 371) of PCT/EP2004/010377 filed Sep. 16, 2004 which claims benefit to German application 103 44 659.1 filed Sep. 25, 2003 and U.S. Provisional application 60/515,922 filed Oct. 29, 2003.

The present invention relates to catalyst systems which can be used for preparing homopolymers or copolymers of olefins and are obtainable by reacting at least one transition metal compound with at least one cocatalyst which is able to convert the transition metal compound into a species which displays polymerization activity toward at least one olefin, wherein the transition metal compound has the formula (I),

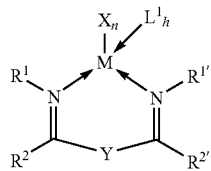

(I)

where

M is an element of group 3, 4, 5, 6, 7, 8, 9 or 10 of the Periodic Table of the Elements or the lanthanides, X are identical or different and are each an organic or inorganic anionic monovalent ligand, where two radicals X may also be joined to form a divalent radical, n is 1, 2, 3 or 4, $L^1$ is an organic or inorganic uncharged ligand, h is an integer from 0 to 4, $R^1$ and $R^{1'}$ can be identical or different and are each hydrogen or an organic radical having from 1 to 40 carbon atoms, $R^2$ and $R^{2'}$ can be identical or different and are each a substituted or unsubstituted $C_6$-$C_{40}$-aryl radical or $C_2$-$C_{40}$-heteroaromatic radical containing at least one heteroatom selected from the group consisting of O, N, S or P, and Y is a divalent group between the two $sp^2$-hybridized carbon atoms and is selected from the group consisting of the two-membered bridges —N($R^3$)—N($R^4$)— and —O—N($R^5$)— and the one-membered bridges —O—, —N($R^6$)—, —N(O$R^7$)— and —N(N$R^8R^9$)—, where $R^3$, $R^4$, $R^5$, $R^6$, $R^7$, $R^8$ and $R^9$ are identical or different and are each hydrogen or an organic radical having from 1 to 40 carbon atoms, where two adjacent radicals may also form a divalent organic group having from 1 to 40 carbon atoms which together with the atom or atoms connecting its ends forms a heterocyclic ring system.

In addition, the present invention relates to the use of such catalyst systems for preparing polyolefins, to a process for preparing polyolefins by polymerization or copolymerization of at least one olefin in the presence of a catalyst system according to the present invention, to the transition metal compounds of the formula (I) themselves, to the use of diimine ligand systems for preparing transition metal compounds and to the preparation of transition metal compounds and specific diimine ligand systems themselves.

Polymers and copolymers of olefins are of great economic importance because the monomers are readily available in large quantities and because the polymers can be varied within a wide range by variation of the production process or the processing parameters. In the production process, particular attention has to be paid to the catalyst used. Apart from Ziegler-Natta catalysts, various single-site catalysts are of increasing importance. In these, central atoms which have been examined in detail include both Zr as in, for example, metallocene catalysts (H.-H. Brintzinger et al., Angew. Chem. 1995, 107, 1255), and Ni or Pd (WO 96/23010) or Fe and Co (e.g. WO 98/27124). The complexes of Ni, Pd, Fe and Co are also referred to as complexes of "late transition metals".

Metallocene catalysts have disadvantages in industrial use. The most frequently used metallocenes, i.e. zirconocenes and hafnocenes, are sensitive to hydrolysis. Furthermore, most metallocenes are sensitive toward many catalyst poisons such as alcohols, ethers or carbon monoxide, which makes careful purification of the monomers necessary.

While Ni or Pd complexes (WO 96/23010) catalyze the formation of highly branched polymers which are of little commercial interest, the use of Fe or Co complexes leads to the formation of highly linear polyethylene having very small proportions of comonomer.

As G. J. P. Britovsek et al. show in Angew. Chem. 1999, 111, 448 and in Angew. Chem. Int. Ed. Engl. 1999, 38, 428, the search for very versatile polymerization-active complexes continues to be of importance because of the great commercial importance of polyolefins. There is interest in finding polymerization-active complexes which have a particularly favorable property profile from a process engineering point of view.

It is an object of the present invention to find novel catalyst systems for the polymerization of olefins which are based on nonmetallocenes, to provide novel complexes which are suitable for the polymerization of olefins to form high molecular weight polymers, to provide a process for preparing the complexes of the present invention and to provide an economical process for the polymerization or copolymerization of olefins using the catalyst systems of the present invention.

We have found that this object is achieved by the catalyst systems mentioned at the outset.

In formula I, the variables are defined as follows:

M is an element of group 3, 4, 5, 6, 7, 8, 9 or 10 of the Periodic Table of the Elements or the lanthanides, for example scandium, yttrium, titanium, zirconium, hafnium, vanadium, niobium, tantalum, chromium, molybdenum, tungsten, manganese, iron, cobalt, nickel or palladium, preferably iron, nickel or palladium, particularly preferably nickel or palladium, in particular nickel.

The radicals X can be identical or different, in particular identical, and are each an organic or inorganic anionic monovalent ligand, where two radicals X may also be linked to form a divalent radical. X is preferably halogen, for example fluorine, chlorine, bromine, iodine, preferably chlorine or bromine, hydrogen, $C_1$-$C_{20}$-, preferably $C_1$-$C_4$-alkyl, $C_2$-$C_{20}$-, preferably $C_2$-$C_4$-alkenyl, $C_6$-$C_{22}$-, preferably $C_6$-$C_{10}$-aryl, an alkylaryl or arylalkyl group having from 1 to 10, preferably from 1 to 4, carbon atoms in the alkyl part and from 6 to 22, preferably from 6 to 10, carbon atoms in the aryl part. X is particularly preferably halogen.

n is 1, 2, 3 or 4, and usually corresponds to the oxidation number of M. Preference is given to n being 2 or 3, in particular 2.

$L^1$ is an organic or inorganic uncharged ligand. Examples of such uncharged ligands are phosphines such as triphenylphosphine, amines such as triethylamine or N,N,N',N'-tetramethylethylenediamine, ethers such as dialkyl ethers, e.g. diethyl ether, or cyclic ethers, e.g. tetrahydrofuran, water, alcohols such as methanol or ethanol, pyridine, pyridine derivatives such as 2-picoline, 3-picoline, 4-picoline, 2,3-lutidine, 2,4-lutidine, 2,5-lutidine, 2,6-lutidine or 3,5-lutidine, carbon monoxide and also $C_1$-$C_{12}$-alkylnitriles or $C_6$-$C_{14}$-arylnitriles such as acetonitrile, propionitrile, butyronitrile or benzonitrile. Furthermore, compounds having one or more ethylenically unsaturated double bonds can also serve as ligand.

h is an integer from 0 to 4.

$R^1$ and $R^{1'}$ can be identical or different, preferably identical, and are each hydrogen or an organic radical having from 1 to 40 carbon atoms.

Preferred examples of such radicals are cyclic, branched or unbranched $C_1$-$C_{20}$-, preferably $C_1$-$C_8$-alkyl radicals, $C_2$-$C_{20}$-, preferably $C_2$-$C_8$-alkenyl radicals, $C_6$-$C_{22}$-, preferably $C_6$-$C_{10}$-aryl radicals, alkylaryl or arylalkyl radicals having from 1 to 10, preferably from 1 to 4, carbon atoms in the alkyl part and from 6 to 22, preferably from 6 to 10, carbon atoms in the aryl part, where the radicals may also be halogenated, or the radicals may also be substituted or unsubstituted, saturated or unsaturated, in particular aromatic, heterocyclic radicals which have from 2 to 40, in particular from 4 to 20 carbon atoms and contain at least one heteroatom, preferably selected from the group consisting of O, N, S and P, in particular N.

Particular preference is given to $R^1$ and $R^{1'}$ each being hydrogen, a cyclic, branched or unbranched $C_1$-$C_8$-alkyl radical, a $C_6$-$C_{10}$-aryl radical, an alkylaryl or arylalkyl radical having from 1 to 4 carbon atoms in the alkyl part and from 6 to 10 carbon atoms in the aryl part or $R^1$ and $R^{1'}$ being five- or six-membered nitrogen-containing heteroaromatics which are bound via a single bond and may be substituted or unsubstituted.

Examples of particularly preferred radicals $R^1$ and $R^{1'}$ are hydrogen, methyl, ethyl, n-propyl, iso-propyl, n-butyl, i-butyl, s-butyl, t-butyl, n-pentyl, cyclopentyl, n-hexyl, cyclohexyl, n-heptyl, n-octyl, benzyl, 2-phenylethyl, phenyl, pentafluorophenyl, 2-tolyl, 3-tolyl, 4-tolyl, 2,3-dimethylphenyl, 2,4-dimethylphenyl, 2,5-dimethylphenyl, 2,6-dimethylphenyl, 2,6-di(isopropyl)phenyl, 3,4-dimethylphenyl, 3,5-dimethylphenyl, 3,5-di(tert-butyl)-phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl, p-trimethylsilylphenyl, N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl; where the last-named nitrogen-containing heterocycles may also bear a substituent such as methyl, ethyl, isopropyl, tert-butyl or phenyl.

Very particular preference is given to $R^1$ and $R^{1'}$ each being a $C_6$-$C_{10}$-aryl radical or an alkylaryl radical having from 1 to 4 carbon atoms in the alkyl part and from 6 to 10 carbon atoms in the aryl part or $R^1$ and $R^{1'}$ being five- or six-membered nitrogen-containing heteroaromatics which are bound via a single bond and may be substituted or unsubstituted. Especial preference is given to $R^1$ and $R^{1'}$ each being a 2,6-di-$C_1$-$C_4$-alkyl-substituted phenyl radical.

$R^2$ and $R^{2'}$ can be identical or different, preferably identical, and are each a substituted or unsubstituted $C_6$-$C_{40}$-aryl radical or a $C_2$-$C_{40}$-heteroaromatic radical containing at least one heteroatom selected from the group consisting of O, N, S and P, in particular N.

$R^2$ and $R^{2'}$ are preferably each a substituted or unsubstituted aryl radical such as phenyl, pentafluorophenyl, 2-tolyl, 3-tolyl, 4-tolyl, 2,3-dimethylphenyl, 2,4-dimethylphenyl, 2,5-dimethylphenyl, 2,6-dimethylphenyl, 2,6-di(isopropyl)phenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl or p-trimethylsilylphenyl.

Y is a divalent group which is located between the $sp^2$-hybridized carbon atoms and is selected from the group consisting of the two-membered bridges —$N(R^3)$—$N(R^4)$— and —$O$—$N(R^5)$— and the one-membered bridges -$O$—, —$N(R^6)$—, —$N(OR^7)$— and —$N(NR^8R^9)$—, preferably the two-membered bridges $N(R^3)$—$N(R^4)$— and —$O$—$N(R^5)$—, where $R^3$, $R^4$, $R^5$, $R^6$, $R^7$, $R^8$ and $R^9$ are identical or different and are each hydrogen or an organic radical having from 1 to 40 carbon atoms, where two adjacent radicals may also form a divalent organic group which has from 1 to 40 carbon atoms and together with the atom or atoms connecting its ends forms a heterocyclic ring system.

Preferred examples of the radicals $R^3$, $R^4$, $R^5$, $R^6$, $R^7$, $R^8$ and $R^9$ are cyclic, branched or un-branched $C_1$-$C_{20}$-, preferably $C_1$-$C_8$-alkyl radicals, $C_2$-$C_{20}$-, preferably $C_2$-$C_8$-alkenyl radicals, $C_6$-$C_{22}$-, preferably $C_6$-$C_{10}$-aryl radicals, alkylaryl or arylalkyl radicals having from 1 to 10, preferably from 1 to 4, carbon atoms in the alkyl part and from 6 to 22, preferably from 6 to 10, carbon atoms in the aryl part, where the radicals may also be halogenated, or the radicals may be substituted or unsubstituted, saturated or unsaturated, in particular aromatic, heterocyclic radicals which have from 2 to 40, in particular from 4 to 20, carbon atoms and contain at least one heteroatom, preferably selected from the group consisting of O, N, S and P, in particular N.

If two adjacent radicals together with the atom or atoms connecting them form a heterocyclic ring system, this is preferably a 4- to 8-membered, in particular 5- or 6-membered, ring system which may be saturated or unsaturated.

According to the present invention, the radicals $R^1$, $R^{1'}$, $R^2$, $R^{2'}$, $R^3$, $R^4$, $R^5$, $R^6$, $R^7$, $R^8$ and $R^9$ can also contain functional groups without altering the polymerization properties of the catalyst system of the present invention, as long as these functional groups are chemically inert under the polymerization conditions.

Furthermore, the substituents according to the present invention are, unless restricted further, defined as follows:

The term "organic radical having from 1 to 40 carbon atoms" as used in the present text refers, for example, to $C_1$-$C_{40}$-alkyl radicals, $C_1$-$C_{10}$-fluoroalkyl radicals, $C_1$-$C_{12}$-alkoxy radicals, saturated $C_3$-$C_{20}$-heterocyclic radicals, $C_6$-$C_{40}$-aryl radicals, $C_2$-$C_{40}$-heteroaromatic radicals, $C_6$-$C_{10}$-fluoroaryl radicals, $C_6$-$C_{10}$-aryloxy radicals, $C_3$-$C_{18}$-trialkylsilyl radicals, $C_2$-$C_{20}$-alkenyl radicals, $C_2$-$C_{20}$-alkynyl radicals, $C_7$-$C_{40}$-arylalkyl radicals or $C_8$-$C_{40}$-arylalkenyl radicals.

The term "alkyl" as used in the present text encompasses linear or singly branched or multiply branched saturated hydrocarbons which may also be cyclic. Preference is given to a $C_1$-$C_{18}$-alkyl, such as methyl, ethyl, n-propyl, n-butyl, n-pentyl, n-hexyl, n-heptyl, n-octyl, n-nonyl, n-decyl, cyclopentyl or cyclohexyl, isopropyl, isobutyl, isopentyl, isohexyl, sec-butyl or tert-butyl.

The term "alkenyl" as used in the present text encompasses linear or singly branched or multiply branched hydrocarbons having one or more C—C double bonds which may be cumulated or alternating.

The term "saturated heterocyclic radical" as used in the present text refers, for example, to monocyclic or polycyclic, substituted or unsubstituted hydrocarbon radicals in which one or more carbon atoms, CH groups and/or CH$_2$ groups are replaced by heteroatoms which are preferably selected from the group consisting of O, S, N and P. Preferred examples of substituted or unsubstituted, saturated heterocyclic radicals are pyrrolidinyl, imidazolidinyl, pyrazolidinyl, piperidyl, piperazinyl, morpholinyl, tetrahydrofuranyl, tetrahydropyranyl, tetrahydrothienyl and the like, and also methyl-, ethyl-, propyl-, isopropyl- and tert-butyl-substituted derivatives thereof.

The term "aryl" as used in the present text refers, for example, to aromatic and fused or unfused polyaromatic hydrocarbon substituents which may be monosubstituted or polysubstituted by linear or branched $C_1$-$C_{18}$-alkyl, $C_1$-$C_{18}$-alkoxy, $C_2$-$C_{10}$-alkenyl or halogen, in particular fluorine. Preferred examples of substituted and unsubstituted aryl radicals are, in particular, phenyl, pentafluorophenyl, 4-methylphenyl, 4-ethylphenyl, 4-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl or 4-trifluoromethylphenyl.

The term "heteroaromatic radical" as used in the present text refers, for example, to aromatic hydrocarbon substituents in which one or more carbon atoms are replaced by nitrogen, phosphorus, oxygen or sulfur atoms or combinations thereof. These may, like the aryl radicals, be monosubstituted or polysubstituted by linear or branched $C_1$-$C_{18}$-alkyl, $C_2$-$C_{10}$-alkenyl or halogen, in particular fluorine. Preferred examples are furyl, thienyl, pyrrolyl, pyridyl, pyrazolyl, imidazolyl, oxazolyl; thiazolyl, pyrimidinyl, pyrazinyl and the like, and also methyl-, ethyl-, propyl-, isopropyl- and tert-butyl-substituted derivatives thereof.

The term "arylalkyl" as used in the present text refers, for example, to aryl-containing substituents whose aryl radical is linked via an alkyl chain to the remainder of the molecule. Preferred examples are benzyl, substituted benzyl, phenethyl, substituted phenethyl and the like.

The terms fluoroalkyl and fluoroaryl mean that at least one, preferably more than one, and at most all hydrogen atoms of the respective substituent are replaced by fluorine atoms. Examples of fluorine-containing substituents which are preferred according to the present invention are trifluoromethyl, 2,2,2-trifluoroethyl, pentafluorophenyl, 4-trifluoromethylphenyl, 4-perfluoro-tert-butylphenyl and the like.

Preference is given to catalyst systems as described above in which the transition metal compound has a formula (I) in which M is Ni or Pd, in particular Ni, X is halogen, for example fluorine, chlorine, bromine or iodine, preferably chlorine or bromine, in particular bromine, n is 2, h is 0, $R^1$ and $R^{1'}$ are identical and are each a substituted or unsubstituted $C_6$-$C_{40}$-aryl radical or a nitrogen-containing heteroaromatic radical having from 4 to 20 carbon atoms, preferably a substituted or unsubstituted $C_6$-$C_{40}$ aryl radical or an alkylaryl radical having from 1 to 10, preferably from 1 to 4, carbon atoms in the alkyl part and from 6 to 22, preferably from 6 to 10, carbon atoms in the aryl part, in particular a phenyl radical substituted by two $C_1$-$C_4$-alkyl radicals in positions 2 and 6, where the radicals may also be halogenated and preferred examples are phenyl, pentafluorophenyl, 2-tolyl, 3-tolyl, 4-tolyl, 2,3-dimethylphenyl, 2,4-dimethylphenyl, 2,5-dimethylphenyl, 2,6-dimethylphenyl, 2,6-di(isopropyl)phenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl and p-trimethylsilylphenyl, in particular 2,6-dimethylphenyl and 2,6-di(isopropyl)phenyl, and the other variables are as defined for the formula (I).

Illustrative but nonlimiting examples of transition metal compounds of the formula (I) which can be used as constituents of catalyst systems of the present invention are:

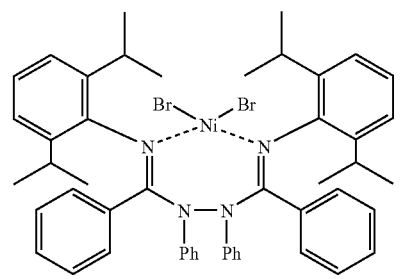

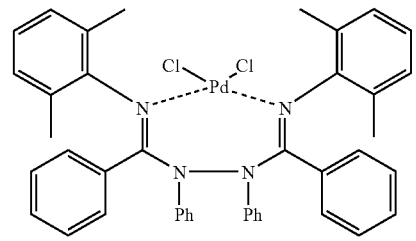

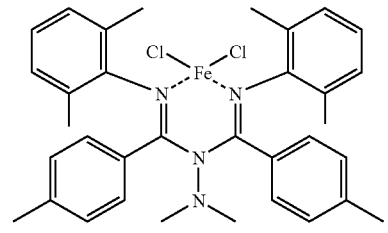

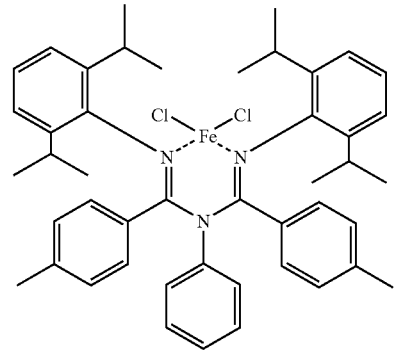

-continued

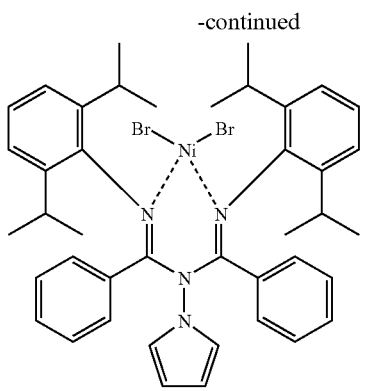

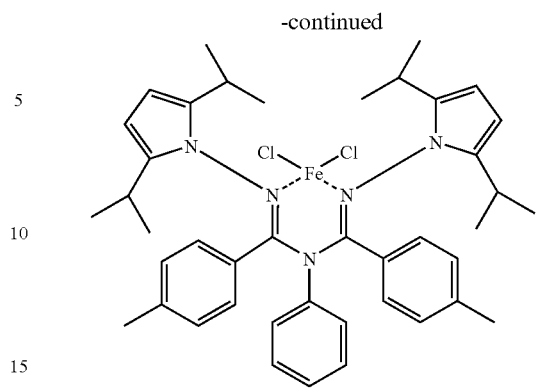

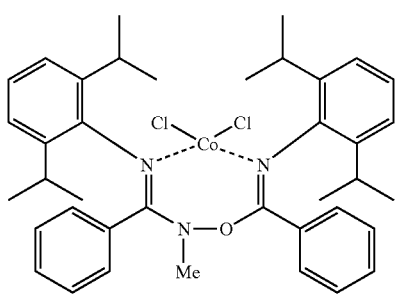

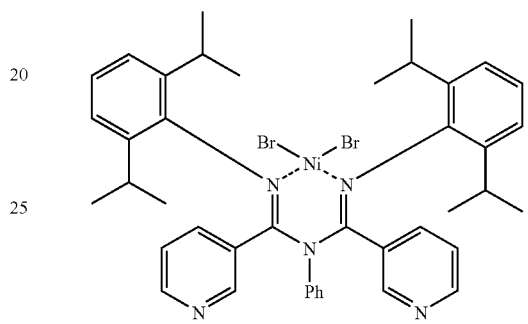

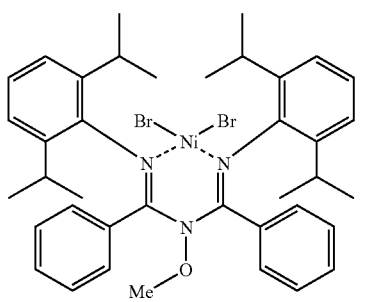

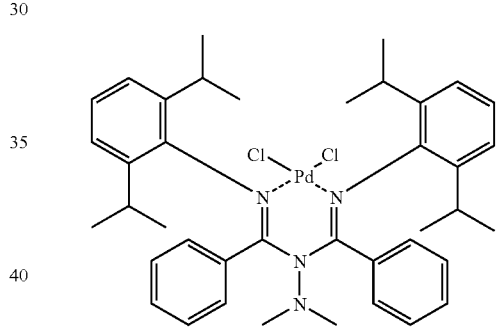

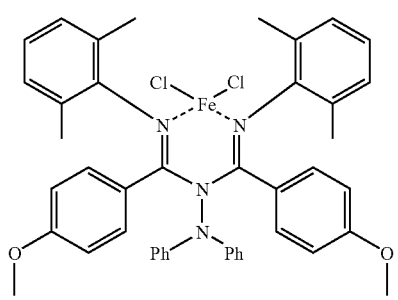

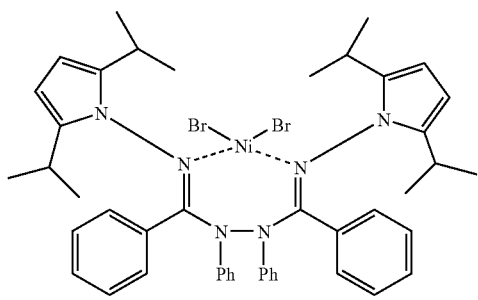

The synthesis of the complexes is known in principle and can be carried out as described in EP 1336615.

The cocatalyst which together with the above-described transition metal compound of the formula (I) forms the polymerization-active catalyst system of the present invention is able to convert the transition metal compound into a species which displays polymerization activity toward at least one olefin. The cocatalyst is therefore sometimes also referred to as activating compound. The polymerization-active transition metal species is frequently a cationic species. In this case, the cocatalyst is frequently also referred to as cation-forming compound.

Suitable catalysts or cation-forming compounds are, for example, aluminoxanes, strong uncharged Lewis acids, ionic compounds having a Lewis-acid cation or ionic compounds containing a Brönsted acid as cation. Preference is given to an aluminoxane as cocatalyst.

Aluminoxanes which can be used are, for example, the compounds described in WO 00/31090. Particularly useful compounds are open-chain or cyclic aluminoxane compounds of the formulae (III) or (IV)

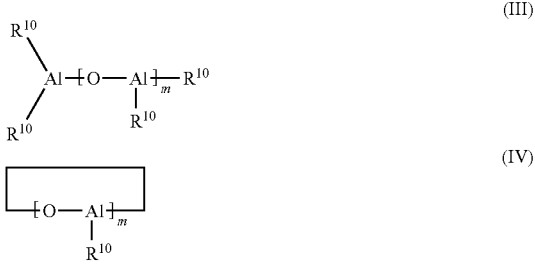

(III)

(IV)

where

R$^{10}$ is a C$_1$-C$_4$-alkyl group, preferably a methyl or ethyl group, and m is an integer from 5 to 30, preferably from 10 to 25.

These oligomeric aluminoxane compounds are usually prepared by reacting a solution of trialkylaluminum with water. In general, the oligomeric aluminoxane compounds obtained in this way are in the form of mixtures of both linear and cyclic chain molecules of various lengths, so that m is to be regarded as a mean. The aluminoxane compounds can also be present in a mixture with other metal alkyls, preferably aluminum alkyls.

Furthermore, modified aluminoxanes in which some of the hydrocarbon radicals or hydrogen atoms have been replaced by alkoxy, aryloxy, siloxy or amide groups can also be used in place of the aluminoxane compounds of the formulae (III) or (IV).

It has been found to be advantageous to use the transition metal compound and the aluminoxane compounds in such amounts that the atomic ratio of aluminum from the aluminoxane compounds to the transition metal from the transition metal compound is in the range from 10:1 to 1000:1, preferably in the range from 20:1 to 500:1 and in particular in the range from 30:1 to 400:1.

As strong, uncharged Lewis acids, preference is given to compounds of the formula (V)

$$M^1X^1X^2X^3 \qquad (V).$$

where

M$^1$ is an element of group 13 of the Periodic Table of the Elements, in particular B, Al or Ga, preferably B, X$^1$, X$^2$ and X$^3$ are each, independently of one another, hydrogen, C$_1$-C$_{10}$-alkyl, C$_6$-C$_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, in particular haloaryl, preferably pentafluorophenyl.

Further examples of strong, uncharged Lewis acids are given in WO 00/31090.

Particular preference is given to compounds of the formula (V) in which X$^1$, X$^2$ and X$^3$ are identical, preferably tris(pentafluorophenyl)borane.

Strong uncharged Lewis acids which are suitable as cocatalyst or cation-forming compounds also include the reaction products from the reaction of a boronic acid with two equivalents of a trialkylaluminum or the reaction products from the reaction of a trialkylaluminum with two equivalents of an acidic fluorinated, in particular perfluorinated, carbon compound such as pentafluorophenol or bis(pentafluorophenyl)borinic acid.

Suitable ionic compounds having Lewis-acid cations include salt-like compounds of the cation of the formula (VI)

$$[(Z^{a+})Q^1Q^2\ldots Q^z]^{d+} \qquad (VI)$$

where

Z is an element of groups 1 to 16 of the Periodic Table of the Elements,

Q$^1$ to Q$^z$ are singly negatively charged groups such as C$_1$-C$_{28}$-alkyl, C$_6$-C$_{15}$-aryl, alkylaryl, arylalkyl, haloalkyl, haloaryl each having from 6 to 20 carbon atoms in the aryl radical and from 1 to 28 carbon atoms in the alkyl radical, C$_3$-C$_{10}$-cycloalkyl, which may bear C$_1$-C$_{10}$-alkyl groups as substituents, halogen, C$_1$-C$_{28}$-alkoxy, C$_6$-C$_{15}$-aryloxy, silyl or mercaptyl groups, a is an integer from 1 to 6 and z is an integer from 0 to 5, and d is the difference a–z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis(pentafluorophenyl)borate.

Salts having noncoordinating anions can also be prepared by adding a boron or aluminum compound, e.g. an aluminum alkyl, to a second compound which can react to link two or more boron or aluminum atoms, e.g. water, and a third compound which forms an ionizing ionic compound with the boron or aluminum compound, e.g. triphenylchloromethane. A fourth compound which likewise reacts with the boron or aluminum compound, e.g. pentafluorophenol, can additionally be added.

Ionic compounds containing Brönsted acids as cations preferably likewise have noncoordinating counterions. As Brönsted acids, particular preference is given to protonated amine or aniline derivatives. Preferred cations are N,N-dimethylanilinium, N,N-dimethylcylohexylammonium and N,N-dimethylbenzylammonium and also derivatives of the latter two.

Preferred ionic compounds as cocatalysts or cation-forming compounds are, in particular, N,N-di-methylanilinium tetrakis(pentafluorophenyl)borate, N,N-dimethylcyclohexylammonium tetrakis(pentafluorophenyl)borate and N,N-dimethylbenzylammonium tetrakis(pentafluorophenyl)borate.

It is also possible for two or more borate anions to be joined to one another, as in the dianion [(C$_6$F$_5$)$_2$B—C$_6$F$_4$—B(C$_6$F$_5$)$_2$]$^{2-}$, or the borate anion can be bound via a bridge having a suitable functional group to the surface of a support particle.

Further suitable cocatalysts or cation-forming compounds are listed in WO 00/31090.

The amount of strong, uncharged Lewis acids, ionic compounds having Lewis-acid cations or ionic compounds containing Brönsted acids as cations is usually from 0.1 to 20 equivalents, preferably from 1 to 10 equivalents, based on the transition metal compound.

Suitable cocatalysts or cation-forming compounds also include boron-aluminum compounds such as di[bis(pentafluorophenylboroxy)]methylalane. Such boron-aluminum compounds are disclosed, for example, in WO 99/06414.

It is also possible to use mixtures of all of the abovementioned cocatalysts or cation-forming compounds. Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl) borane.

Preference is given to using both the transition metal compound and the cocatalysts or cation-forming compounds in a solvent, with aromatic hydrocarbons having from 6 to 20 carbon atoms, in particular xylenes and toluene, being preferred.

The catalyst system of the present invention can further comprise a metal compound of the formula (VII),

$$M^2(R^{11})_r(R^{12})_s(R^{13})_t \quad (VII)$$

where $M^2$ is an alkali metal, an alkaline earth metal or a metal of group 13 of the Periodic Table of the Elements, i.e. boron, aluminum, gallium, indium or thallium, $R^{11}$ is hydrogen, $C_1$-$C_{10}$-alkyl, $C_6$-$C_{15}$-aryl, alkylaryl or arylalkyl each having from 1 to 10 carbon atoms in the alkyl part and from 6 to 20 carbon atoms in the aryl part, $R^{12}$ and $R^{13}$ are identical or different and are each hydrogen, halogen, $C_1$-$C_{10}$-alkyl, $C_6$-$C_{15}$-aryl, alkylaryl, arylalkyl or alkoxy each having from 1 to 10 carbon atoms in the alkyl radical and from 6 to 20 carbon atoms in the aryl radical, r is an integer from 1 to 3, and s and t are integers from 0 to 2, where the sum r+s+t corresponds to the valence of $M^2$, where the metal compound of the formula (VII) is usually not identical to the cocatalyst or the cation-forming compound. It is also possible to use mixtures of various metal compounds of the formula (VII).

Among the metal compounds of the formula (VII), preference is given to those in which $M^2$ is lithium, magnesium or aluminum and $R^{12}$ and $R^{13}$ are each $C_1$-$C_{10}$-alkyl.

Particularly preferred metal compounds of the formula (VII) are n-butyllithium, n-butyl-n-octyl-magnesium, n-butyl-n-heptylmagnesium, tri-n-hexylaluminum, triisobutylaluminum, triethylaluminum and trimethylaluminum and mixtures thereof.

If a metal compound of the formula (VII) is used, it is preferably present in the catalyst system of the present invention in such an amount that the molar ratio of $M^2$ from the formula (VII) to transition metal from the transition metal compound of the formula (I) is from 800:1 to 1:1, in particular from 200:1 to 2:1.

The catalyst system of the present invention particularly preferably further comprises a support.

To obtain such a supported catalyst system, the unsupported catalyst system can be reacted with a support. In principle, the order in which the support, the transition metal compound and the cocatalyst are combined is immaterial. The transition metal compound and the cocatalyst can be immobilized independently of one another or simultaneously. After the individual process steps, the solid can be washed with a suitable inert solvent, e.g. an aliphatic or aromatic hydrocarbon.

As supports, preference is given to using finely divided supports which can be any organic or inorganic, inert solids. In particular, the support can be a porous solid such as talc, a sheet silicate, an inorganic oxide or a finely divided polymer powder (e.g. polyolefin).

Suitable inorganic oxides may be found among oxides of the elements of groups 2, 3, 4, 5, 13, 14, 15 and 16 of the Periodic Table of the Elements. Examples of oxides preferred as supports include silicon dioxide, aluminum oxide and mixed oxides of the elements calcium, aluminum, silicon, magnesium and/or titanium and also corresponding oxide mixtures. Other inorganic oxides which can be used either alone or in combination with the abovementioned preferred oxidic supports are, for example, MgO, $ZrO_2$, $TiO_2$ or $B_2O_3$. An example of a preferred mixed oxide is calcined hydrotalcite.

The support materials used preferably have a specific surface area in the range from 10 to 1 000 $m^2/g$, a pore volume in the range from 0.1 to 5 ml/g and a mean particle size of from 1 to 500 µm. Preference is given to supports having a specific surface area in the range from 50 to 500 $m^2/g$, a pore volume in the range from 0.5 to 3.5 ml/g and a mean particle size in the range from 5 to 350 µm. Particular preference is given to supports having a specific surface area in the range from 200 to 400 $m^2/g$, a pore volume in the range from 0.8 to 3.0 ml/g and a mean particle size of from 10 to 100 µm.

The inorganic support can be subjected to a thermal treatment, e.g. to remove adsorbed water. Such a drying treatment is generally carried out at from 80 to 300° C., preferably from 100 to 200° C., with drying at from 100 to 200° C. preferably being carried out under reduced pressure and/or under a blanket of inert gas (e.g. nitrogen), or the inorganic support can be calcined at from 200 to 1000° C. in order to obtain the desired structure of the solid and/or the desired OH concentration on the surface. The support can also be treated chemically using customary desiccants such as metal alkyls, preferably aluminum alkyls, chlorosilanes or $SiCl_4$ or else methylaluminoxane. Appropriate treatment methods are described, for example, in WO 00/31090. The inorganic support material can also be modified chemically. For example, treatment of silica gel with $(NH_4)_2SiF_6$ to fluorinate the silica gel surface or treatment of silica gels with silanes containing nitrogen-, fluorine- or sulfur-containing groups leads to appropriately modified silica gel surfaces.

Organic support materials such as finely divided polyolefin powders (e.g. polyethylene, polypropylene or polystyrene) can also be used and are preferably likewise freed of adhering moisture, solvent residues or other impurities by means of appropriate purification and drying operations before use. It is also possible to use functionalized polymer supports, e.g. supports based on polystyrenes via whose functional groups, for example ammonium or hydroxy groups, at least one of the catalyst components can be immobilized.

In a preferred embodiment of the preparation of the supported catalyst system of the present invention, at least one transition metal compound of the formula (I) is brought into contact with at least one cocatalyst as activating or cation-forming compound in a suitable solvent, giving a soluble or insoluble, preferably soluble, reaction product, an adduct or a mixture.

The composition obtained in this way is then mixed with the dehydrated or passivated support material, the solvent is removed and the resulting supported transition metal catalyst system is dried to ensure that all or most of the solvent is removed from the pores of the support material. The supported catalyst is obtained as a free-flowing powder. Examples of the industrial implementation of the above process are described in WO 96/00243, WO 98/40419 or WO 00/05277.

A further preferred embodiment comprises firstly applying the cocatalyst or the cation-forming compound to the support component and subsequently bringing this supported cocatalyst or cation-forming compound into contact with the transition metal compound.

Further cocatalyst systems which are of importance therefore likewise include combinations obtained by combining the following components:

1st component: at least one defined boron or aluminum compound,
2nd component: at least one uncharged compound which has at least one acidic hydrogen atom,
3rd component: at least one support, preferably an inorganic oxidic support, and optionally, as 4th component, a base, preferably an organic nitrogen-containing base, for example an amine, an aniline derivative or a nitrogen heterocycle.

The boron or aluminum compounds used in the preparation of the supported cocatalysts are preferably compounds of the formula (VIII)

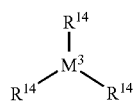
(VIII)

where
$R^{14}$ are identical or different and are each hydrogen, halogen, $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl or $R^{14}$ is an $OSiR^{15}{}_3$ group, where
$R^{15}$ are identical or different and are each hydrogen, halogen, $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, preferably hydrogen, $C_1$-$C_8$-alkyl or $C_7$-$C_{20}$-arylalkyl, and
$M^3$ is boron or aluminum, preferably boron.

Particularly preferred compounds of the formula (VIII) are trimethylaluminum, triethylaluminum and triisobutylaluminum.

The uncharged compounds which have at least one acidic hydrogen atom and can react with compounds of the formula (VIII) are preferably compounds of the formula (IX), (X) or (XI),

(IX)

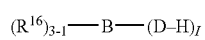
(X)

(XI)

where
$R^{16}$ are identical or different and are each hydrogen, halogen, a boron-free $C_1$-$C_{40}$ group such as $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, an $Si(R^{18})_3$ group or a $CH(SiR^{18}{}_3)_2$ group, where
$R^{18}$ is a boron-free $C_1$-$C_{40}$ group such as $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, and
$R^{17}$ is a divalent $C_1$-$C_{40}$ group such as $C_1$-$C_{20}$-alkylene, $C_1$-$C_{20}$-haloalkylene, $C_6$-$C_{20}$-arylene, $C_6$-$C_{20}$-haloarylene, $C_7$-$C_{40}$-arylalkylene, $C_7$-$C_{40}$-haloarylalkylene, $C_7$-$C_{40}$-alkylarylene, $C_7$-$C_{40}$-haloalkylarylene, D is an element of group 16 of the Periodic Table of the Elements or an $NR^{19}$ group, where $R^{19}$ is hydrogen or a $C_1$-$C_{20}$ hydrocarbon radical such as $C_1$-$C_{20}$-alkyl or $C_6$-$C_{20}$-aryl, preferably D is oxygen, and
i is 1 or 2.

Suitable compounds of the formula (IX) include water, alcohols, phenol derivatives, thiophenol derivatives and aniline derivatives, with halogenated and especially perfluorinated alcohols and phenols being of particular importance. Examples of particularly useful compounds are pentafluorophenol, 1,1-bis(pentafluorophenyl)methanol and 4-hydroxy-2,2',3,3',4',5,5',6,6'-nonafluorobiphenyl.

Suitable compounds of the formula (X) include boronic acids and borinic acids, in particular borinic acids having perfluorinated aryl radicals, for example $(C_6F_5)_2BOH$.

Suitable compounds of the formula (XI) include dihydroxy compounds in which the divalent carbon-containing group is preferably halogenated and in particular perfluorinated. An example of such a compound is 4,4'-dihydroxy-2,2',3,3',5,5',6,6'-octafluorobiphenyl hydrate.

Examples of combinations of compounds of the formula (VIII) with compounds of the formula (IX) or (XI) are trimethylaluminum/pentafluorophenol, trimethylaluminum/1-bis(pentafluorophenyl)methanol, trimethylaluminum/4-hydroxy-2,2',3,3',4',5,5',6,6'-nonafluorobiphenyl, triethylaluminum/pentafluorophenol or triisobutylaluminum/pentafluorophenol and triethylaluminum/4,4'-dihydroxy-2,2',3,3',5,5',6,6'-octafluorobiphenyl hydrate, with, for example, reaction products of the following type being able to be formed:

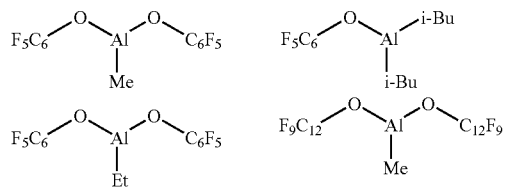

Examples of reaction products of the reaction of at least one compound of the formula (VIII) with at least one compound of the formula (X) are:

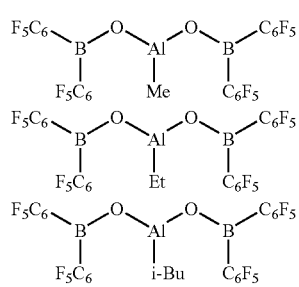

The order in which the components are combined is in principle immaterial.

If desired, the reaction products from the reaction of at least one compound of the formula (VIII) with at least one compound of the formula (IX), (X) or (XI) and optionally an organic nitrogen base are additionally combined with an organometallic compound of the formula (III), (IV), (V) and/or (VII) before being combined with the support to form the supported cocatalyst system.

In a preferred variant, the 1st component, e.g. compounds of the formula (VIII), is combined with the 2nd component, e.g. compounds of the formula (IX), (X) or (XI), and a support as 3rd component is combined with a base as 4th component and the two mixtures are subsequently reacted with one another, preferably in an inert solvent or suspension medium. The supported cocatalyst formed can be freed of the inert solvent or suspension medium before it is reacted with the transition metal compound of the formula (I) and, if desired, a metal compound of the formula (VII) to form the catalyst system of the present invention.

It is also possible for the catalyst solid of the present invention firstly to be prepolymerized with α-olefins, preferably linear $C_2$-$C_{10}$-1-alkenes and in particular ethylene or propylene, and the resulting prepolymerized catalyst solid then to be used in the actual polymerization. The mass ratio of catalyst solid used in the prepolymerization to monomer polymerized onto it is usually in the range from 1:0.1 to 1:200.

Furthermore, a small amount of an olefin, preferably an α-olefin, for example vinylcyclohexane, styrene or phenyidimethylvinylsilane, as modifying component, an antistatic or a suitable inert compound such as a wax or oil can be added as additive during or after the preparation of the supported catalyst system of the present invention. The molar ratio of additives to transition metal compound is usually from 1:1000 to 1000:1, preferably from 1:5 to 20:1.

The novel catalyst systems based on the above-described transition metal compounds of the formula (I) have the advantage that the transition metal compounds used can readily be synthesized with a wide variety of substitution patterns.

The invention further provides, firstly, for the use of a novel catalyst system as described above for preparing polyolefins and, secondly, a process for preparing polyolefins by polymerization or copolymerization of at least one olefin in the presence of a novel catalyst system as described above.

In general, the catalyst system of the present invention is used together with a further metal compound of the formula (VII), which may be different from the metal compound or compounds of the formula (VII) used in the preparation of the catalyst system of the present invention, for the polymerization or copolymerization of olefins. The further metal compound is generally added to the monomer or suspension medium and serves to free the monomer of substances which could impair the catalyst activity. It is also possible for one or more further cocatalytic or cation-forming compounds to be additionally added to the catalyst system of the present invention in the polymerization process.

The olefins can be functionalized, olefinically unsaturated compounds such as ester or amide derivatives of acrylic or methacrylic acid, for example acrylates, methacrylates or acrylonitrile, or nonpolar olefinic compounds, including arylsubstituted α-olefins.

Preference is given to polymerizing olefins of the formula $R'''$—CH=CH—$R''$, where $R'''$ and $R''$ are identical or different and are each hydrogen or an organic radical having from 1 to 20 carbon atoms, in particular from 1 to 10 carbon atoms, or $R'''$ and $R''$ together with the atoms connecting them can form one or more rings.

Examples of such olefins are 1-olefins having from 2 to 40, preferably from 2 to 10, carbon atoms, e.g. ethylene, propylene, 1-butene, 1-pentene, 1-hexene, 1-heptene, 1-octene, 1-decene or 4-methyl-1-pentene, or unsubstituted or substituted vinyl aromatic compounds such as styrene and styrene derivatives, or dienes such as 1,3-butadiene, 1,4-hexadiene, 1,7-octadiene, 5-ethylidene-2-norbornene, norbornadiene, ethylnorbornadiene or cyclic olefins such as norbornene, tetracyclododecene or methylnorbornene. Preference is given to ethylene, propylene, 1-butene, 1-hexene or 4-methyl-1-pentene.

The catalyst system of the present invention is particularly preferably used for homopolymerizing ethylene or copolymerizing ethylene with further α-olefins, in particular $C_3$-$C_8$-α-olefins such as propylene, 1-butene, 1-pentene, 1-hexene and/or 1-octene and/or cyclic olefins such as norbornene and/or dienes having from 4 to 20 carbon atoms, e.g. 1,4-hexadiene, norbornadiene, ethylidenenorbornene or ethylnorbornadiene. Very particular preference is given to copolymerizing ethylene with propylene and/or 1-butene. Examples of such copolymers are ethylene-propylene, ethylene-1-butene, ethylene-1-hexene, ethylene-1-octene copolymers, ethylene-propylene-ethylidenenorbornene or ethylene-propylene-1,4-hexadiene terpolymers.

The polymerization can be carried out in a known manner in bulk, in suspension, in the gas phase or in a supercritical medium in the customary reactors used for the polymerization of olefins. It can be carried out batchwise or preferably continuously, in one or more stages. Solution processes, suspension processes, stirred gas phase processes or gas-phase fluidized-bed processes are all possible. As solvent or suspension medium, it is possible to use inert hydrocarbons, for example isobutane, or else the monomers themselves.

The polymerization can be carried out at from −60 to 300° C. and pressures in the range from 0.5 to 3000 bar. Preference is given to temperatures in the range from 50 to 200° C., in particular from 60 to 150° C., very particularly preferably from 70° C. to 120° C., and pressures in the range from 5 to 100 bar, in particular from 15 to 70 bar. The mean residence times are usually from 0.5 to 5 hours, preferably from 0.5 to 3 hours. Hydrogen can be used in the polymerization as molar mass regulator and/or to increase the activity. Furthermore, customary additives such as antistatics can also be used. The catalyst system of the present invention can be used directly for the polymerization, i.e. it is introduced in pure form into the polymerization system, or it is admixed with inert components such as paraffins, oils or waxes to improve meterabilty.

The catalyst systems of the present invention are especially useful for preparing homopolymers and copolymers of ethylene.

The catalysts of the present invention can also be used together with one or more other polymerization catalysts known per se. Thus, for example, they can be used together with Ziegler-Natta catalysts, supported metallocene catalysts containing transition metals of groups 4 to 6 of the Periodic Table of the Elements, Catalysts derived from the late transition metals (WO 96/23010), Fe or Co complexes with pyridyidiimine ligands as are disclosed in WO 98/27124, or chromium oxide catalysts of the Phillips type.

It is possible either to mix various catalysts with one another and meter them in together or to use cosupported complexes on a common support or else to meter various catalysts separately into the polymerization vessel at the same point or at different points.

The invention further provides transition metal compounds of the formula (I)

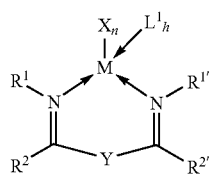

where the variables are as defined above.

The invention further provides for the use of a ligand system of the formula (II)

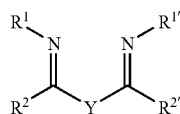

for preparing a transition metal compound, preferably for preparing a transition metal compound of nickel or palladium, in particular nickel, where the variables are as defined for the formula (I).

Thus, the present invention also provides a process for preparing a transition metal compound, which comprises reacting a ligand system of the formula (II) with a transition metal compound. The uncharged diimine ligand system is usually reacted with a suitable transition metal compound, preferably a transition metal halide such as nickel (II) bromide, in a suitable solvent or suspension medium.

The invention further provides a ligand system of the formula (II) in which the variables $R^1$, $R^{1'}$, $R^2$ and $R^{2'}$ are as defined for the formula (I) and Y is —N($R^3$)—N($R^4$)— or —O—N($R^5$)—, where $R^3$, $R^4$ and $R^5$ are as defined under the formula (I).

The substitution pattern of the diimine ligands of the formula (II) is of critical importance for the polymerization properties of the transition metal compounds containing these diimine ligands and the same transition metal ion M.

One possible way of preparing the ligand, namely reacting an imide chloride with a suitable bridging reagent, is known and is described, for example, in J. Org. Chem., Vol. 36, No. 8, 1971, pages 1155-1158.

The invention is illustrated by the following nonlimiting examples.

EXAMPLES

General Preliminary Remarks

All work was, unless indicated otherwise, carried out in the absence of air and moisture using standard Schlenk techniques. Apparatus and chemicals were prepared appropriately. The polymer viscosity was determined in accordance with ISO 1628-3.

Preparation of the Ligands

1) Preparation of N-(2,6-diisopropylphenyl)-N'-[[(2,6-diisopropylphenyl)imino]phenylmethoxy]-N'-methylbenzamidine (1)

a) Preparation of the imide chloride N-(2,6-diisopropylphenyl)benzimide chloride (1a)

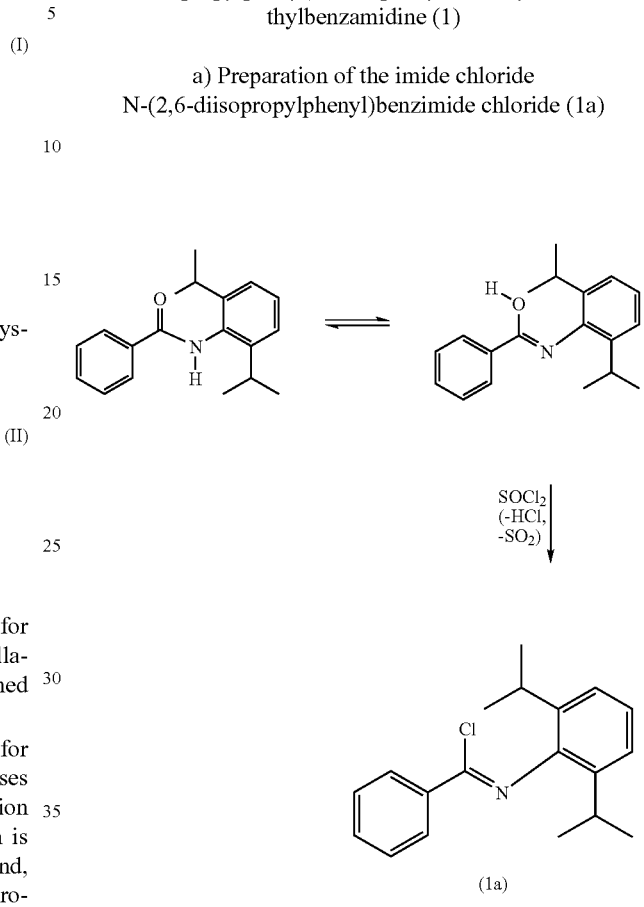

1.9 g of N-(2,6-diisopropylphenyl)benzamide (6.7 mmol) were placed in a dry Schlenk tube which had been flushed with argon. After addition of 10 ml of thionyl chloride, the reaction solution was refluxed for 60 minutes. Excess thionyl chloride was taken off under a high vacuum, and the yellow oil which remained (compound 1a) was dissolved in 20 ml of methylene chloride (absolute).

b) Preparation of N-(2,6-diisopropylphenyl)-N'-[[(2,6-diisopropylphenyl)imino]phenylmethoxy]-N'-methylbenzamidine (1)

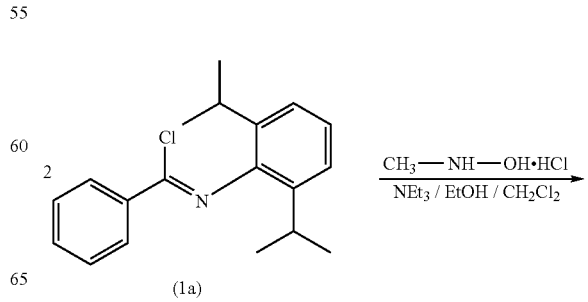

-continued

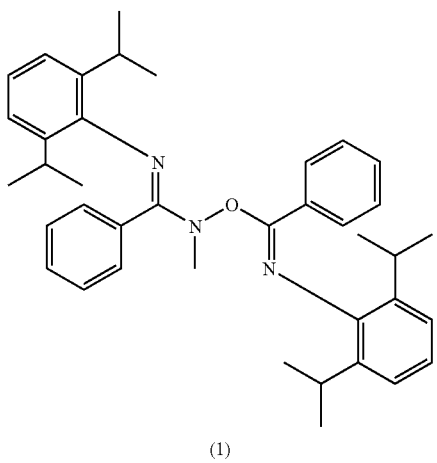

(1)

N-Methylhydroxylamine hydrochloride (0.28 g, 3.35 mmol) was placed in a baked Schienk tube which had been flushed with argon and was dissolved in absolute ethanol (50 ml). After addition of 10 ml of triethylamine (72 mmol), the resulting suspension was cooled to 40° C. The imide chloride (1a) which had been prepared under a) and dissolved in methylene chloride was slowly added from a dropping funnel to the solution b) at −40° C. over a period of 30 minutes. After warming to room temperature, the reaction mixture (yellow suspension) was stirred for 1 hour. Subsequent monitoring by means of thin layer chromatography (diethyl ether) indicated complete conversion: a nonpolar component which moved with the solvent front and a polar starting spot were obtained. The reaction mixture was poured into water (about 100 ml), and the product was extracted three times with 50 ml each time of ether. The organic phase was dried over $Na_2SO_4$ and the desiccant was filtered off. After the solvent had been taken off on a rotary evaporator, the resulting semicrystalline solid was dissolved in small amounts of methylene chloride and filtered through a silica gel bed. The nonpolar component which was very readily soluble in ether was in this way completely separated from the polar component. Removal of the solvent and recrystallization gave 1.6 g of (1) as a yellow solid.

$^1$HNMR (CDCl$_3$): 1.14-1.21 (24H, m, 4×CH(C$\underline{H}_3$)$_2$), 3.10, 3.42 (4H, sept, 4×C$\underline{H}$(CH$_3$)$_2$), 6.46 (2H, pseudo-d, phenyl), 6.91-7.90 (16H, m, phenyl)

$^{13}$C NMR (CDCl$_3$): 22.0, 23.7, 24.0 (CH(C$\underline{H}_3$)$_2$), 28.9 ($\underline{C}$H(CH$_3$)$_2$), 39.7 (N—CH$_3$), 122.9, 123.7, 127.1, 127.8, 127.9, 128.5, 128.8, 129.0, 129.3, 130.4 (C-phenyl), 131.8, 133.1, 142.1, 143.5, 146.4 (C-phenyl, quaternary C), 154.5, 160.4 (C=N)

IR (KBr, cm$^{-1}$): 2970 (m), 2931 (m), 2869 (m), 1683 (vs), 1630 (vs), 1602 (m), 1590 (m), 1578 (m), 1492 (m), 1459 (m), 1436 (m), 1407 (w), 1383 (m), 1362 (w), 1328 (m), 1287 (w), 1264 (m), 1233 (m), 1185 (w), 1108 (m), 1063 (s), 1038 (m), 1030 (m), 1013 (vs), 922 (w), 803 (m), 766 (s), 726 (m)

MS (FAB): [M+H]$^+$=574.4 m/e

2) Preparation of N-(2,6-dimethylphenyl)-N'-methyl-N'-[(2,6-dimethylphenyl)imino]-phenylmethoxy]benzamidine (2)

a) Preparation of the imide chloride N-(2,6-dimethylphenyl)benzimide chloride (2a)

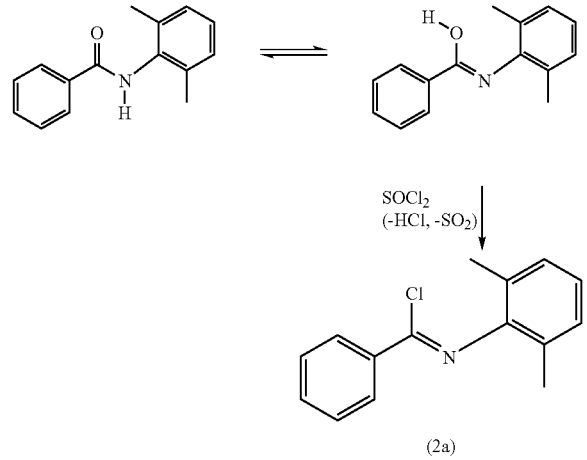

(2a)

2.3 g of N-(2,6-dimethylphenyl)benzamide (10.2 mmol) were placed in a dry Schlenk tube which had been flushed with argon. After addition of 10 ml of thionyl chloride, the reaction solution was refluxed for 60 minutes. Excess SOCl$_2$ was taken off under a high vacuum, and the yellow oil which remained (compound 2a) was dissolved in 20 ml of methylene chloride (absolute).

b) Preparation of N-(2,6-dimethylphenyl)-N'-methyl-N'-[(2,6-dimethylphenyl)imino]-phenylmethoxy]benzamidine (2)

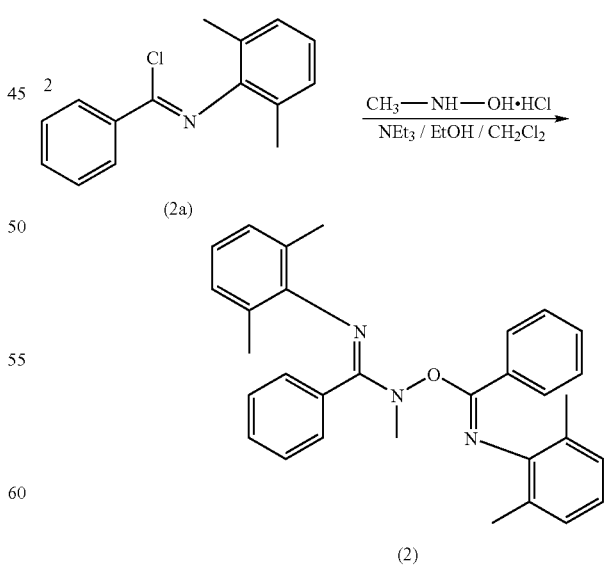

N-methylhydroxylamine hydrochloride (0.43 g, 5.1 mmol) was placed in a baked Schlenk tube which had been flushed with argon and was dissolved in absolute ethanol (40 ml).

After addition of 10 ml of triethylamine (72 mmol), the resulting suspension was cooled to −40° C. The imide chloride (2a) which had been prepared under a) and dissolved in methylene chloride was slowly added from a dropping funnel to the solution b) at −40° C. over a period of 30 minutes. After warming to room temperature, the reaction mixture (yellow suspension) was stirred for 1 hour. Subsequent monitoring by means of thin layer chromatography (diethyl ether) indicated complete conversion: a nonpolar component (2) which moved with the solvent front and a polar starting spot (by-product) were observed.

The reaction mixture was poured into water (about 100 ml) and the product was extracted three times with 50 ml each time of ether. After the aqueous phase had been neutralized, it was extracted again with ether (2×40 ml). The combined organic phases were dried over $Na_2SO_4$ and the desiccant was filtered off. After the solvent had been taken off on a rotary evaporator, the resulting semicrystalline solid was dissolved in small amounts of methylene chloride and filtered through a silica gel bed. The nonpolar component (2) which was very readily soluble in ether was separated completely from the polar component in this way. Removal of the solvent and crystallization gave 2.2 g of (2) as a yellow solid.

$^1$H NMR ($CDCl_3$): 1.95, 2.20 (12H, 2×s, 4×$CH_3$), 3.61 (3H, s, N—$CH_3$), 6.52 (2H, pseudo-d, phenyl), 6.67-6.96 (7H, m, phenyl), 7.05-7.22 (5H, m, phenyl), 7.41 (2H, pseudo-d, phenyl)

$^{13}$C NMR ($CDCl_3$): 18.5, 18.8 ($CH_3$), 39.4 (N—$CH_3$), 122.3, 122.9, 127.0, 127.1, 127.6, 127.8, 127.9, 128.2, 128.7, 129.4, 129.5, 130.0, 130.5 (C-phenyl), 131.7, 133.6, 135.5 (quaternary C, phenyl), 144.6, 146.1 (C=N—C, quaternary C, phenyl), 154.7, 161.5 (C=N, quaternary C)

IR (KBr, $cm^{-1}$): 2919 (w), 1688 (vs), 1644 (vs), 1592 (m), 1580 (w), 1493 (w), 1466 (m), 1447 (m), 1405 (w), 1326 (s), 1293 (w), 1262 (m), 1246 (m), 1229 (m), 1216 (m), 1183 (w), 1104 (w), 1079 (s), 1069 (s), 1027 (m), 1013 (w), 922 (w), 787 (m), 768 (vs), 756 (m), 741 (m), 697 (vs), 675 (m)

MS: $M^+$=461.3 m/e

3) Preparation of N-(2,6-diisopropylphenyl)-N'-[[[(2,6-diisopropylphehyl)imino]benzyl]-phenylamino] benzamidine (3)

a) Preparation of the imide chloride N-(2,6-diisopropylphenyl)benzimide chloride (1a)

(1a) was prepared from 2.03 g of N-(2,6-diisopropylphenyl) benzamide (7.2 mmol) and thionyl chloride using a method analogous to Example 1a).

b) Preparation of N-(2,6-diisopropylphenyl)-N'-[[[(2,6-diisopropylphenyl)imino]benzyl]-phenylamino] benzamidine (3)

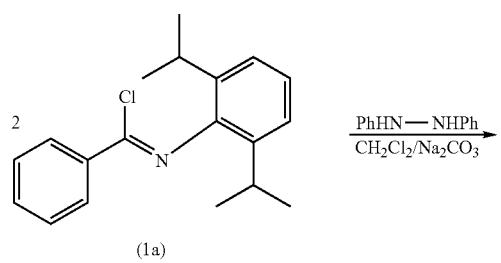

(1a)

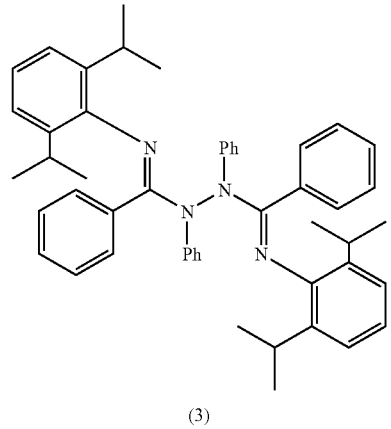

(3)

The symmetrically substituted N,N'-diphenylhydrazine (0.70 g, 3.8 mmol) was placed in a baked Schlenk tube which had been flushed with argon and was suspended in 20 ml of methylene chloride (abs). 1.87 g of $Na_2CO_3$ (18 mmol) were added.

After the reaction solution had been cooled to −70° C., the imide chloride from experiment 3a) dissolved in methylene chloride was slowly added from a dropping funnel over a period of 30 minutes. After removing the cold bath, the mixture was stirred at room temperature for 1 hour. Checking the progress of the reaction by means of TLC (ether/hexane=⅓) showed that the reaction was complete.

The reaction mixture was poured into water (about 100 ml) and the product was extracted three times with 50 ml each time of diethyl ether. To improve phase separation, 50 ml of saturated sodium chloride solution were added. The combined organic phases were dried over $Na_2SO_4$ and the desiccant was filtered off. After the solvent had been taken off on a rotary evaporator, the resulting viscous oil was dried in a high vacuum and was subsequently recrystallized from an ethyl acetate/hexane solvent mixture: (3) was obtained as a yellow solid in a yield of 0.9 g.

$^1$H NMR ($CDCl_3$): 1.00 (12H, d, 2×CH($CH_3$)$_2$, J=6.6 Hz), 1.25 (12H, d, 2×CH($CH_3$)$_2$, J=6.6 Hz), 3.13 (4H, sept, 4×C$H$($CH_3$)$_2$), 6.92 (4H, d, phenyl), 7.04 (8H, pseudo-t, phenyl), 7.13-7.36 (14H, m, phenyl)

$^{13}$C NMR ($CDCl_3$): 21.7, 25.5 (CH($CH_3$)$_2$), 28.9 ($H$($CH_3$)$_2$), 123.8, 124.5, 124.6, 124.9, 127.5, 128.6, 128.8, 129.1, 129.3, 129.5, 129.7 (C-phenyl), 132.6 (quaternary C, phenyl), 135.3 (N=C—C, quaternary C, phenyl), 137.9 (N—C, quaternary C, phenyl), 145.3 (C=N—C, quaternary C, phenyl), 164.9 (C=N, quaternary C)

IR (KBr, $cm^{-1}$): 2964 (m), 2929 (m), 2869 (m), 1627 (vs), 1607 (s), 1589 (m), 1574 (s), 1497 (m), 1463 (m), 1443 (w), 1356 (w), 1328 (m), 1104 (w), 1057 (w), 1007 (w), 822 (w), 805 (w), 789 (w), 778 (w), 762 (w), 700 (m)

MS (FAB): $[M+H]^+$=711.5 m/e.

Synthesis of Complexes

C1 Preparation of N-(2,6-diisopropylphenyl)-N'-[[[(2,6-diisopropylphenyl)imino]benzyl]-phenylamino]benzamidinenickel(II) dibromide (C1)

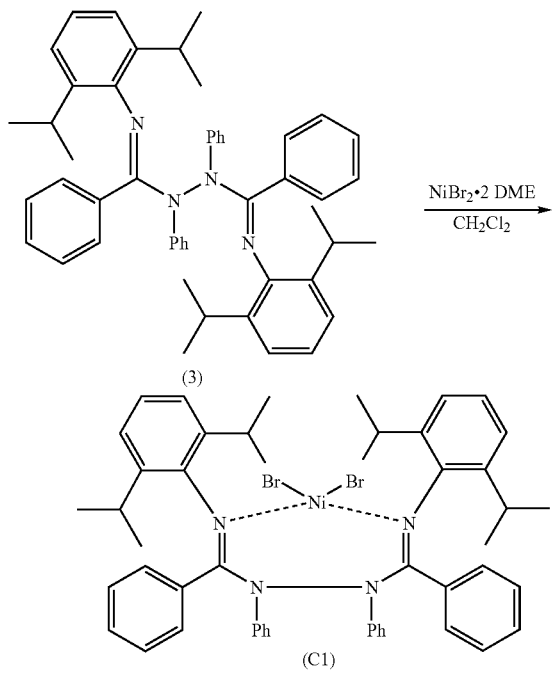

The uncharged di(imino)-[N,N] ligand (3) (0.26 g, 0.37 mmol) was placed in a dry Schlenk tube which had been flushed with argon, dissolved in 20 ml of methylene chloride (absolute) and, after addition of the dimethoxyethane-stabilized transition metal halide (NiBr$_2$×2 DME, 0.17 g, 0.40 mmol, 1.1 meq), stirred overnight at room temperature (immediate complex formation with color change from yellow→green).

The solution was evaporated to dryness in a high vacuum, and 0.3 g of a pulverulent, light-green complex (C1) was isolated.

$^1$H NMR (CD$_2$Cl$_2$): 1.07 (12H, d, 2×CH(C$\underline{H}_3$)$_2$, J=6.9 Hz), 1.31 (12H, d, 2×CH(C$\underline{H}_3$)$_2$, J=6.6 Hz), 3.14 (4H, sept, 4×C$\underline{H}$(CH$_3$)$_2$), 6.97 (5H, d, phenyl), 7.09 (8H, d, phenyl), 7.18-7.30 (7H, m, phenyl), 7.34-7.39 (6H, m, phenyl)

$^{13}$C NMR (CD$_2$Cl$_2$): 21.8, 26.7 (CH($\underline{C}$H$_3$)$_2$), 29.5 ($\underline{C}$H(CH$_3$)$_2$), 124.2, 125.1, 125.3, 125.4, 127.5, 127.9, 128.1, 129.1, 129.2, 129.7, 129.8 (C-phenyl), 130.2, 133.1, 135.5, 138.4 (quaternary C, phenyl), 145.9 (C=N—$\underline{C}$, quaternary C, phenyl), 165.5 (C=N).

Polymerization Experiments

Example P1

1.8 mg of the complex (C1) from Example C1, 2 ml of 30% strength by weight MAO solution in toluene (commercially available from Witco) and 400 ml of toluene were placed in a 1 l steel auto-clave which had been made inert. At 70° C., ethylene was injected to a pressure of 40 bar. This pressure was kept constant during the polymerization time of 90 minutes by introduction of further ethylene. The reaction was stopped by venting and the polymer was isolated by filtration, subsequent washing with methanol and drying under reduced pressure. This gave 1.7 g of polymer having a viscosity of 2.5 dl/g.

We claim:

1. A transition metal compound of the formula (I)

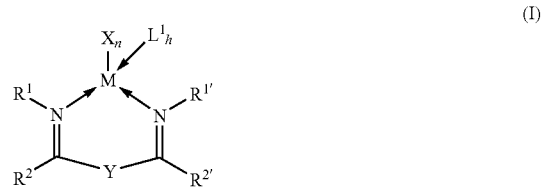

where
M is an element of group 3, 4, 5, 6, 7, 8, 9 or 10 of the Periodic Table of the Elements or the lanthanides,
X are identical or different and are each an organic or inorganic anionic monovalent ligand, where two radicals x may also be joined to form a divalent radical,
n is 1, 2, 3 or 4,
L$^1$ is an organic or inorganic uncharged ligand,
h is an integer from 0 to 4,
R$^1$ and R$^{1'}$ can be identical or different and are each hydrogen or an organic radical having from 1 to 40 carbon atoms,
R$^2$ and R$^{2'}$ can be identical or different and are each a substituted or unsubstituted C$_6$-C$_{40}$-aryl radical or C$_2$-C$_{40}$-heteroaromatic radical containing at least one heteroatom selected from the group consisting of O, N, S and P,
and
Y is a divalent group between the two sp$^2$-hybridized carbon atoms and is selected from the group consisting of the two-membered bridges —N(R$^3$)—N(R$^4$)— and —O—N(R$^5$)— and the one-membered bridges —O—, —N(R$^6$)—, —N(OR$^7$)— and —N(NR$^8$R$^9$)—,
where
R$^3$, R$^4$, R$^5$, R$^6$, R$^7$, R$^8$ and R$^9$ are identical or different and are each hydrogen or an organic radical having from 1 to 40 carbon atoms, where two adjacent radicals may also form a divalent organic group having from 1 to 40 carbon atoms which together with the atom or atoms connecting its ends forms a heterocyclic ring system.

2. A process for preparing a transition metal compound, which comprises reacting a transition metal compound with a ligand system of the formula (II)

where
R$^1$ and R$^{1'}$ can be identical or different and are each hydrogen or an organic radical having from 1 to 40 carbon atoms,
R$^2$ and R$^{2'}$ can be identical or different and are each a substituted or unsubstituted C$_6$-C$_{40}$-aryl radical or C$_2$-C$_{40}$-heteroaromatic radical containing at least one heteroatom selected from the group consisting of O, N, S and P,
and Y is a divalent group between the two $sp^2$-hybridized carbon atoms and is selected from the group consisting of the two-membered bridges —$N(R^3)$—$N(R^4)$— and —O—$N(R^5)$— and the one-membered bridges —O—, —$N(R^6)$—, —$N(OR^7)$— and —$N(NR^8R^9)$—, where $R^3$, $R^4$, $R^5$, $R^6$, $R^7$, $R^8$ and $R^9$ are identical or different and are each hydrogen or an organic radical having from 1 to 40 carbon atoms, where two adjacent radicals may also form a divalent organic group having from 1 to 40 carbon atoms which together with the atom or atoms connecting its ends forms a heterocyclic ring system.

\* \* \* \* \*